United States Patent [19]

Wolff

[11] 4,287,554

[45] Sep. 1, 1981

[54] RADIATION APPARATUS

[76] Inventor: Friedrich Wolff, Lindenring 17, D-6000 Frankfurt 60, Fed. Rep. of Germany

[21] Appl. No.: 53,515

[22] Filed: Jun. 29, 1979

[30] Foreign Application Priority Data

Jul. 3, 1978 [DE] Fed. Rep. of Germany ....... 2829117
Oct. 24, 1978 [DE] Fed. Rep. of Germany ....... 2846221

[51] Int. Cl.³ .............................................. F21S 2/00
[52] U.S. Cl. .................................. 362/218; 362/225; 362/240; 362/241; 362/349; 362/293; 362/294
[58] Field of Search .................. 362/293, 2, 218, 225, 362/240, 241, 349, 294

[56] References Cited

U.S. PATENT DOCUMENTS 4,091,441  5/1978  Ott .......................................... 362/2

Primary Examiner—Stephen J. Lechert, Jr.
Attorney, Agent, or Firm—Peter K. Kontler

[57] ABSTRACT

Apparatus for producing ultraviolet radiation, particularly a quick-tanning or therapeutic sunlamp, has a source of substantially uniform ultraviolet radiation, including at least two closely adjacent tubular low-pressure mercury lamps; an arrangement for intercepting at least the major percentage of wavelength bands of ultraviolet radiation below approximately 300 mm; and a reflector system cooperating with said source and defining at least one opening for the escape of ultraviolet radiation consisting essentially of the remaining wavelength band of ultraviolet radiation, said reflector system including for each of said lamps a trough-shaped reflector surrounding the lamp along an arc, and at least one intermediate portion between adjacent ones of said lamps and two lateral portions having zones which project forwardly of said intermediate portion and have forward edge portions defining said opening, the space between said lateral portions and forwardly of said intermediate portion being substantially unobstructed, and the source and reflector system cooperating to establish in the vicinity of the opening a high-density radiation field, the heat output of said lamps being sufficiently low so that the temperature in the region of said radiation field is below the range of discomfort of a person exposed to the field. The apparatus may include a mirror flanked by the lamps so that a user can enjoy the benefits of the ultraviolet radiation at no additional expenditure of time while looking into the mirror for other purposes.

35 Claims, 7 Drawing Figures

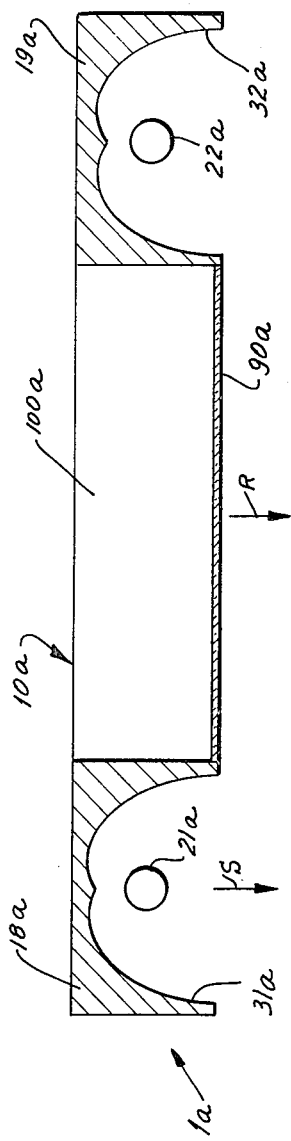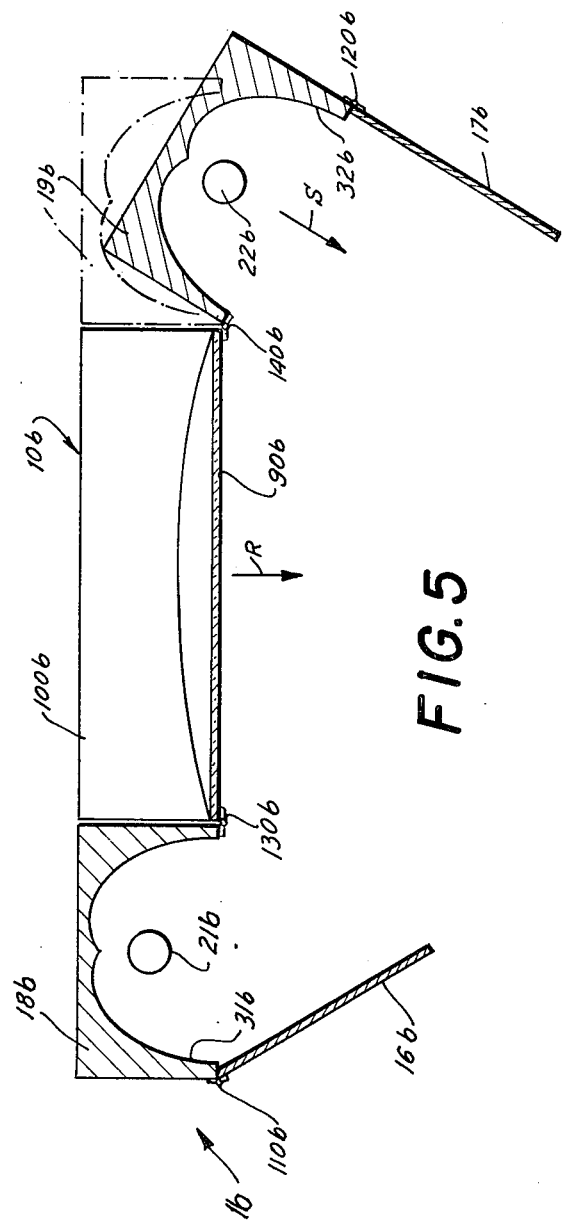

RADIATION APPARATUS

BACKGROUND OF THE INVENTION

The present invention relates to radiation apparatus in general, and more particularly, to apparatus for producing radiation predominantly in the ultraviolet range of the spectrum. Specifically, the invention relates to apparatus for producing ultraviolet radiation for medical or theraputic applications such as treatment of psoriasis, and/or for cosmetic applications such as quick tanning or portions of the human body.

An apparatus of this general type is known from U.S. Pat. No. 4,095,113, the contents of which is incorporated herein by reference. In that apparatus a series of at least five (and as many as twenty) low-pressure mercury lamps of rod-shaped configuration is arranged in parallel, with each lamp being located in a trough-shaped reflector. The apparatus produces at its outlet a substantially uniform high-density ultraviolet radiation field. A filter intercepts at least the major percentage of the ultraviolet radiation bands below approximately 315 nm (in the so-called UVC range of 200 to 280 nm and UVB range of 280 to 315 nm), so that the field coming in contact with the body of a user consists essentially of the remaining waveband length of ultraviolet radiation, that is, in the UVA range of 315 to 400 nm and at most in a bordering portion of the UVB range.

This apparatus has been found to be highly efficacious for administering treatments to the human body without causing discomfort and burning, e.g., during quick tanning of the skin. A special advantage of this apparatus over any other prior-art apparatus emitting radiation in a wider portion of the ultraviolet range of the spectrum is that a person to be irradiated can assume a position at or in close proximity of the outlet of the apparatus. This is possible because the lamps of the above-mentioned type produce only a minimum amount of heat which is quickly and easily dissipated into the ambient atmosphere, and because the UVB radiation, which could cause a sunburn, is largely absent from the radiation reaching the person being irradiated. As a result of this, relatively large doses of UVA radiation can be applied to selected parts of the body of the user of this apparatus, and relatively short periods of time are required for achieving a pronounced suntan.

However, its use is practical only for the treatment of large parts of the human body, for example the front or the back of a person. In many instances it is merely necessary to treat smaller parts of the body, e.g., the face or an arm, either to effect tanning or for medical purposes (e.g. to treat psoriasis, acne and other skin irregularities or diseases). In the latter instance, the prior-art apparatus is less than fully effective, particularly since the filter largely intercepts radiation within the 300 to 315 nm portion of the UVB range, which is most effective for these purposes. The conventional apparatus is also too large and expensive for such limited applications, since much of the radiation emitted by it will be wasted when only a small body part is to be treated. Also, if the body part to be treated is strongly rounded—as is the case with e.g., the face (including the cheeks and ears) and arms and legs—, the prior art apparatus generally can be successfully used only if the user is resigned to undergoing repeated treatments in each of which the body part is made to assume a different orientation with respect to the emitted radiation field. Furthermore, the apparatus is absolutely useless unless somebody sets aside the required period of time, however short, and utilizes this period for subjecting his or her body to the radiation emitted by this apparatus in its energized condition. In many instances, this conventional apparatus stands idle for days or even weeks, or is being used by only some but not by other prospective users, simply because all or the other of the prospective users do not find, or do not devote, for reasons of inconvenience or preoccupation with other affairs, the time to the use of this apparatus. This, of course, is very disadvantageous, particularly since this apparatus constitutes a substantial investment which is lost if the apparatus is not being used for its intended purpose, and since the appearance (skin color) or general health (because of the beneficial or therapeutic effect of the ultraviolet radiation) of the prospective user are not improved if he or she does not use this apparatus.

SUMMARY OF THE INVENTION

It is a general object of the invention to avoid the disadvantages of the prior art.

A more particular object of the invention is to provide an apparatus of the type in question, which is especially suited for the treatment of smaller body parts, such as the face, arms and legs of a user.

Another object is to provide such an apparatus which requires a minimum amount of time and energy to effect the desired treatments.

Still a further object is to provide an apparatus of the type in question which is simple in its construction and highly reliable in its operation.

A concomitant object of the invention is to so construct the apparatus as to be fully effective both for cosmetic and for medical or therapeutic purposes.

Yet another object of the present invention is to develop an apparatus of the type here under consideration which does not require any additional time for achieving the desired irradiation.

In pursuance of these objects, and of others which will become apparent hereafter, one feature of the invention resides in an apparatus for producing ultraviolet radiation, particularly—but not exclusively—a quick-tanning sunlamp. Briefly stated, such apparatus may comprise a source of substantially uniform ultraviolet radiation, including at least one tubular low-pressure mercury lamp; means for intercepting at least the major percentage of wavelength bands of ultraviolet radiation below approximately 300 nm; and reflector means cooperating with the source and defining at least one opening for the escape of ultraviolet radiation consisting essentially of the remaining wavelength band of ultraviolet radiation. Advantageously, the apparatus includes at least two of said lamps which are closely adjacent to one another, and the reflector means includes for each of the lamps a trough-shaped reflector surrounding the lamp along an arc. The reflector means includes at least one intermediate portion between adjacent ones of the lamps and two lateral portions having zones which project forwardly of the intermediate portion and have forward edge portions defining the opening, the space between the lateral portions and forwardly of the intermediate portion being substantially unobstructed and the source and reflector means cooperating to establish in the vicinity of the opening a high-density radiation field, the heat output of the lamps being sufficiently low so that the temperature in the region of the radiation field is below the range of discomfort of a person exposed to the field.

The apparatus according to the invention may advantageously have up to four of the mercury lamps, in which case it will have three of the intermediate reflector portions. More than four of the lamps would make the apparatus uneconomical to construct and operate (loss of radiation past the body part being treated). The apparatus will, however, operate completely satisfactorily with as few as two of the lamps.

Because it has only two, or at most four, of the mercury lamps, the apparatus according to the invention is simple and can be produced quite inexpensively. Furthermore, the loss of unused radiation past the body part to be treated is eliminated or at least minimized, since the body part can be at least partially positioned in the free space between the zones of the lateral reflector portions, i.e. the space which is defined forwardly of the intermediate portion or portions. Moreover, because of the presence of the zones of the lateral portion which extend forwardly beyond the intermediate portion, the radiation is directed against the body part not only from the front, but also from the sides thereof. This means that even strongly rounded body parts (e.g. the face and cheek, an arm, or the like) can be exposed to beneficial radiation in a single treatment over a large surface area, including portions which could not be reached by the front-radiating prior apparatus unless the body portion was repeatedly turned and each newly exposed surface portion was subjected to a new radiation treatment. Accordingly, the number of radiation treatments can be correspondingly smaller with the novel apparatus. Nevertheless, the apparatus according to the invention can also be used with advantage for the radiation treatment of larger body portions (e.g. the chest) which are positioned at a small spacing from its outlet opening, because the forwardly extending parts of the lateral reflector portions prevent dissipation of the radiation and concentrate the radiation field at and in the vicinity of the outlet opening.

Another feature of the present invention resides in the provision of a mirror or a similar light-reflective portion in the housing, the mirror extending beyond the source by a distance which is sufficient for a user of the apparatus to view his or her face in this mirror. Then, it is advantageous to so arrange the mirror relative to the lamp (and possibly also to a reflector which may be arranged behind the lamp as viewed through the opening of the support means) that at least a predominant portion of the radiation emitted by the lamp propagates in a direction substantially parallel to the main reflection direction of the mirror.

In an irradiating apparatus of this type, the irradiation takes place during that period of time which is spent by the respective individual in front of the mirror. Inasmuch as the time spent in front of a mirror (while men shave, women attend to their makeup and people regardless of their gender comb their hair or brush their teeth) amounts to many minutes a day, and in view of the fact that even short time intervals are sufficient for achieving a tanning effect, the desired result is achieved without any additional expenditure of time. This measure is especially intended for the irradiation of the face and/or of the upper part of the body of the user.

It is further advantageous when the ultraviolet radiation has a compontent which is directed toward the mirror. This is especially recommended when the mirror has a considerable width.

In order to achieve an exposure to the radiation which is symmetrical to the greatest achievable extent, it is proposed by the present invention to use at least two of the above-mentioned lamps arranged at opposite sides of the mirror so as to flank the same. However, the same or even better tanning effect is achieved when a lamp is used which has an annular (toroidal) configuration and surrounds the mirror from all sides. When two straight lamps are used, they can be arranged at the vertical sides of the mirror and extend substantially vertically, or at the top and bottom sides of the mirror and extend substantially horizontally; it is further contemplated by the present invention to use four of such straight lamps and to arrange two of them at the vertical, and the remaining two at the horizontal sides of the mirror. Lamps of shapes different from these discussed above could also be used to advantage.

In many instances, it is advantageous to use a concave spherical mirror as the above-mentioned mirror or reflecting portion. It is well known that such a concave mirror has an enlarging effect, but that the user of this mirror has to locate his or her face within a certain, very limited range which is situated relatively close in front of the concave mirror, in order to be able to observe his or her face in such a mirror. As a result of this predetermined position which the face of the user has to assume and which is relatively close not only to the mirror but also to the lamps producing the ultraviolet radiation, the density or intensity of the radiation reaching the face of the user is correspondingly large and it is also correspondingly easy to direct the radiation of the lamps into this limited range.

As already mentioned above, a trough-shaped reflector can be associated with each of the lamps, and the main reflection direction of this reflector may have a component directed toward the mirror. In other words, the main reflection direction of the reflector (at each cross-section thereof) may enclose an acute angle with the plane of the opening of the support means, or with the plane of the mirror, provided that the latter is planar. In this manner, the UVA radiation is diverted from the laterally arranged lamps even to the region of the central plane or axis of the mirror. This can be achieved by so arranging the respective reflector in the housing that it is inclined relative thereto about the center line of the associated lamp. However, it is also possible to use a straight reflector which, however, is mounted, together with its associated lamp, in a part of the housing which is pivotally mounted on the remainder of the housing, particularly in a housing part which is mounted on that part of the housing which includes the mirror for pivoting about an axis parallel to the center line of the trough-shaped reflector. This renders it possible to accurately direct the radiation onto the face or similar part of the body of the user.

It is particularly advantageous when the housing includes a mounting portion and two of the above-mentioned housing parts each of which is mounted on one of the sides of the mounting portion and has a width substantially corresponding to one-half of the width of the housing. In this manner, the aformentioned housing parts can be pivoted into their respective closed or inoperative positions in which they are both located frontwardly of the mounting portion and cover up the interior of the latter. Thus, the housing obtains a visually appealing parallelepiped or columnar configuration for its period of non-use.

Furthermore, or instead, the housing could be equipped, in accordance with a further facet of the present invention, with lateral walls which extend frontwardly of the opening of the housing, these lateral walls being provided with internal surfaces which face the opening and which are reflective at least to ultraviolet radiation. The otherwise lost laterally proceeding dispersion radiation can be salvaged in this manner and redirected into the region of interest which is located frontwardly of the mirror. In the process, even the lateral zones of the face of the user will be subjected to the effects of ultraviolet radiation.

The reflecting lateral walls can be hingedly or pivotally connected to the remainder of the housing, so that they can be pivoted, for the period of non-use, into positions in which they do not disturbingly extend to the front of the housing proper. When each of these lateral walls has a width substantially corresponding to one-half of the width of the mounting portion of the housing, there is again obtained an apparatus having a very compact and esthetically appealing configuration at least when out of use.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 4 is a horizontal sectional view through the apparatus of FIG. 3;

FIG. 5 is a view similar to FIG. 4 but of a further modification of the apparatus;

DESCRIPTION OF THE PREFERRED EMBODIMENTS

Figure 1:
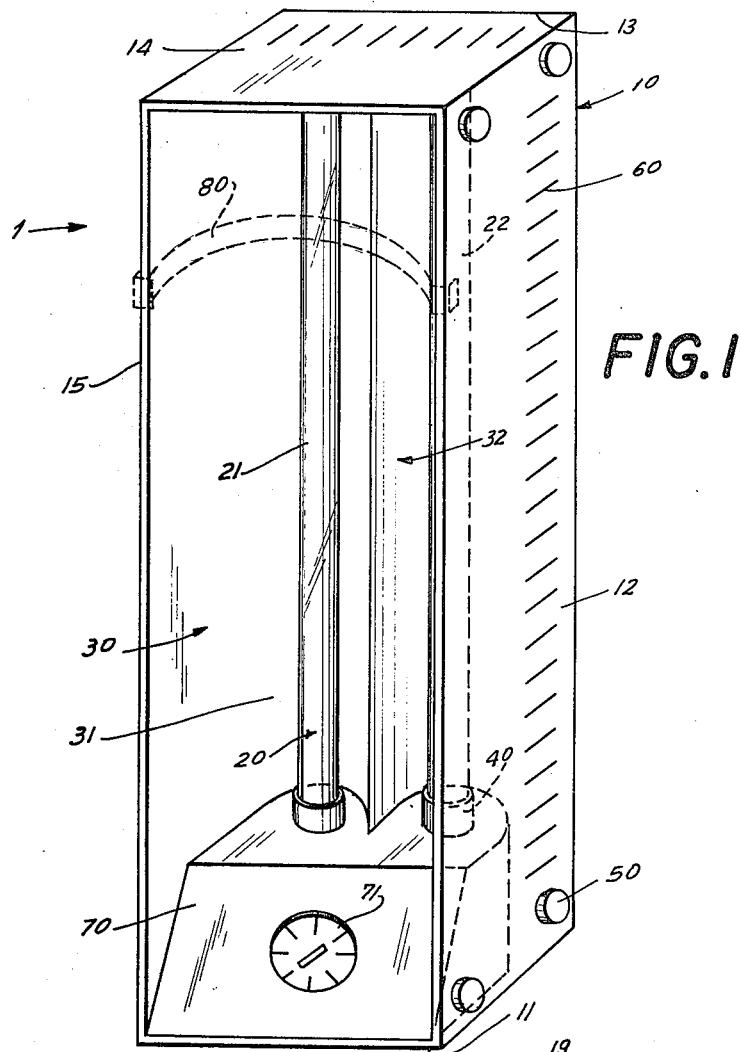
FIG. 1 is a perspective view, showing an apparatus according to the invention.

Referring now to the drawing in detail, and first to FIG. 1, it may be seen that the reference numeral 1 has been used to identify the apparatus of the invention in its entirety. The apparatus 1 has a housing 10. Mounted in the housing 10 in mountings 40 which are conventional and thus have not been shown in detail in a source 20 of ultraviolet radiation, including two parallel tubular low-pressure mercury lamps 21 and 22. When the lamps 21 and 22 are electrically energized, a luminescence layer 23 (shown only in FIG. 2) of each of the lamps 21 and 22 is excited so that it yields ultraviolet radiation having its maximum concentration in the UVA range of upwardly of 315 nm. The lamps 21 and 22 have glass envelopes 24 which are constructed as filters which intercept at least the major percentage of the UVB and UVC wavelengths bands, i.e., the bands below approximately 315 nm when the apparatus is to be used as a quick-tanning lamp, so that skin burns are avoided. Such lamps and filters are described in U.S. Pat. No. 4,095,113, to which reference may be had. However, if the apparatus is to be used for medical or therapeutic purposes, the envelopes 24 are made of a material which, instead or preferably in addition to the UVA radiation, lets at least a predominant portion of wavelengths between substantially 300 to 315 nm pass therethrough. Such materials are well known and commercially available.

The source 20 has associated with it reflector means 30 including a trough-shaped reflector 31, 32 respectively associated with the lamps 21 and 22. The reflectors 31 and 32 may be discrete or of one piece and together they constituted the reflector means 30. They will subsequently be more fully described.

The usually lower end of the housing 10 contains a box or enclosure 70, in which a timer 71 is mounted. The timer 71 may be calibrated from 0 to about 25 or 30 minutes. The timer 71 may simply be an alarm timer which rings or otherwise attracts the attention of a user when the preselected time has elapsed; in that case, the apparatus is provided with a manually operable on-off switch. Alternatively, the timer 71 may be of the type which controls the operation of the lamps 21, 22; i.e., which switches them on when the time is turned from its zero setting and switches them off when it returns to its zero setting. Such timers are known per se, as are the electrical connections between the lamps 21, 22, the source of electrical energy, and the timer 71, and therefore no details need be illustrated, except for diagrammatically showing the sockets 40 in which the upper and lower ends of the lamps 21, 22 are removably held.

The housing 10 and the reflector means 30 including the reflectors 31, 32 may be discrete components of the apparatus defining with one another a ventilation (i.e. cooling) space which communicates with the ambient atmosphere via ports 60 which may be slot-shaped (as shown) or have other shapes. The housing 10 is preferably of parallelepiped configuration, as illustrated, so that it will have several surfaces with which it can rest on a substrate. In FIG. 1 these are a bottom face 11, a side face 12, a rear face 13, a top face 14, and another side face 15. Legs or protuberances 50 may be provided on one or more of these surfaces 11, 12, 13, 14 or 15 to prevent blockage of the ports 60 when a surface, such as the side face 12, of the housing 10 which is provided with such ports 60 faces the substrate or any other adjacent structure.

Figure 2:
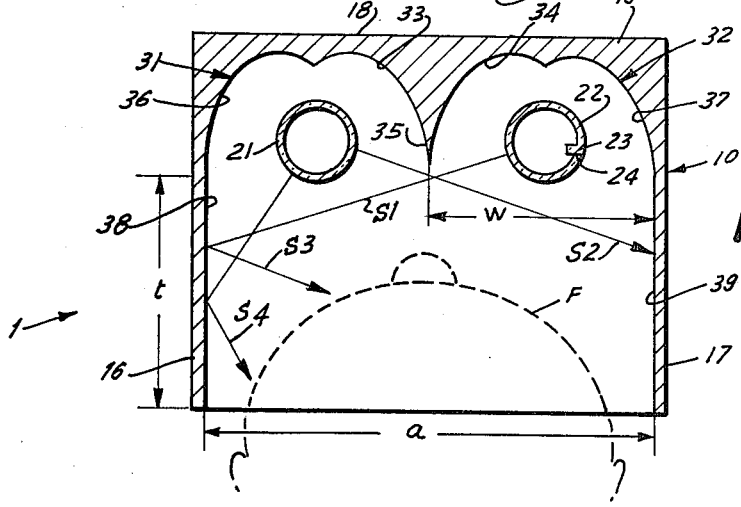
FIG. 2 is a horizontal sectional view through a modified apparatus of FIG. 1.

FIG. 2 shows that the reflector means 30 may be formed as a part of the inner surface of the housing 10 of the apparatus, instead of being separate therefrom as discussed above. If the housing is solid as shown, that is, without any cooling space therein, the ports 60 are omitted. In all other respects, the apparatus shown in FIGS. 1 and 2 is identical.

The trough-shaped reflectors 31 and 32 of the reflector means 30 are formed in portions 18 and 19 of the housing 10 and they hve, in cross section, two arcuate inner wall portions 33 and 34 which together define an intermediate reflector portion 35 that is located between the lamps 21 and 22. The reflectors 31 and 32 further have laterally outer wall portions 36 and 37 which merge into straight, planar zones 38 and 39, respectively, which are formed on portions 16 and 17 of the housing 10. These zones 38 and 39 extend parallel to one another and project forwardly beyond the intermediate portion 35 defined by the two inner wall portions 33 and 34 by a depth t which is slightly greater than the maximum width w of the trough-shaped reflectors 31 and 32.

The outer wall portions 36 and 37 each merge at their inner ends under respective obtuse angles into the laterally outer ends of the inner arcuate portions 33 and 34. The merger line between the portions 33 and 36, and between the portions 34 and 37, coincides in each case with a longitudinal center line (line of symmetry) of the respective reflector 31 and 32 constituted by these portions. The inner ends of the inner arcuate portions 33 and 34 merge with the intermediate portion 35 and this merger line is located at the longitudinal line of symmetry of the reflectors 31, 32 of reflector means 30.

The distance a between the zones 38, 39 is somewhat greater than the width of a human face F, indicated in dashed lines in FIG. 2, i.e. between about 17 and about 20 cm. The depth, as considered from front to back of the housing 10, of the intermediate portion 35 formed by the wall portions 33, 34 is short enough so that at least most of the surface area of the zones 38, 39 can be impinged by direct radiation from the respectively laterally remote lamp 22, 21. In other words, the zone 38 can be impinged by direct radiation from lamp 32 and the zone 39 by direct radiation from lamp 31, as indicated by the arrows S1, S2. Thus, direct radiation at a forward angle (i.e. toward the outlet opening between the free edges of the zones 38 and 39) will be present in the free space between the zones 38 and 39 forwardly of the intermediate portion 35 together with direct forward radiation aimed towards the outlet opening (i.e. radiation parallel to the zones 38, 39).

It is evident, therefore, that a body portion (e.g. the face F of a head H of a user which is illustrated in broken lines in FIG. 2) which is inserted into this free space, will be subjected to the direct radiation from the lamps 21 and 22. In addition, however, those portions of the direct radiation which do not impinge upon the face F, i.e. which pass laterally beyond it and impinge the zones 38 and 39, are reflected by these zones 38 and 39 and, depending upon their angles of incidence and reflection, either also impinge the face F (as indicated by arrow S3) or impinge the body part relatively far rearwardly, e.g. in the case of the face F on the cheeks or ears (as indicated by the arrow S4). Thus, even a strongly curved body portion such as a face, an arm or a leg, will be subjected to radiation over a large part of its surface area, including parts which do not face the source of radiation and would not, in prior-art radiation devices, receive any treatment at all. Of course, the radiation exiting rearwardly from the lamps 21, 22 is reflected by the arcuate portions 33, 34, 36 and 37 of the reflector means 30 and then also impinges the body portion, either directly or upon undergoing renewed reflection from one of the zones 38, 39. The disclosed reflector means 30 thus utilizes substantially all of the radiation of the lamps 21, 22 for the intended purpose and waste due to radiation loss is effectively eliminated.

The apparatus according to the invention, regardless of its structure, may also be provided with one or more preferably arcuate members or brackets 80 (one shown in phantom lines in FIG. 1). These brackets 80 may be secured, releasably or permanently (e.g. by clips, screws, soldering, welding, or the like) to the apparatus 10 across the outlet opening of the same, and serve to position a body part, e.g. an arm, in a precisely predefined position relative to the device. This is especially advantageous if the apparatus is used for dermatological treatments, particularly for the treatment of psoriasis, acne, eczema, or for any other theraputic purposes since affected portions of a body part (e.g. arm) can thus be positioned precisely in the region of greatest strength of the radiation field, approximately at the plane of symmetry of the apparatus and at a predetermined distance from the lamps 21, 22.

The spacing a between the zones 38, 39 could be different from that of a human face. However, the indicated distance of about 17-20 cm makes the device well suited for the treatment of face, arms and legs, i.e. of those body portions for which it is primarily intended.

The zones 38, 39 need not extend parallel to one another. This is, however, of advantage because it offers excellent accessibility of the free space defined between them. Also, it assures that the radiation is reflected under the smallest possible angles, so that the field of ultraviolet radiation is well defined and concentrated upon the area in which the body portions will be located. The overlapping of the radiation from the two lamps within the free space bounded by the zones 38, 39 produces a particularly strong field in this relatively large free space, a factor which is of importance for rapid tanning and for successful medical treatments of e.g. psoriasis.

It goes without saying that the reflector means 30 could have a shape different from that illustrated in FIGS. 1 and 2, as long as the hereinbefore described free space is obtained and the radiation field is concentrated in this free space and in an area somewhat outside but adjacent to the outlet opening of the free space. The reflector means may, of course, be of any suitable material, such as metal or synthetic plastic material (e.g. synethetic plastic material on which the surface that is to act as a reflector has been made reflective by deposition of a reflective layer of coating, e.g. by vapor deposition or sputtering deposition of a metallic coating).

The housing 10 need not have the illustrated shape, although this is especially advantageous since it allows the unit to be used standing on end (e.g. to treat a face), or to rest on one of its side faces or on the rearface (e.g. to treat an arm or a leg). The unit can then be placed into whichever position is most convenient and comfortable for the user when treating a particular body portion.

The housing 10, also, may be made of various different materials. For example, it may be made of metal and produced by stamping, punching, extrusion or the like. If it is of metal, the housing 10 itself may act as a heat sink for heat radiated by the lamps, since such heat is radiated by the housing 10 to the ambient atmosphere. This is especially true when a portion of the housing itself (see FIG. 2) constitutes the reflector means 30. However, in some circumstances—these include the use of discrete reflector means 30 separate from the housing 10—or the use of a housing 10, of e.g. synthetic plastic material (vinyl, polystyrene) which has a low coefficient of thermal transmissivity, the use of the ventilation or cooling space discussed with reference to FIG. 1 will be preferred. In any case, the heat developed during operation of the source 20 is very low, so that problems do not develop in connection with its dissipation. This is the reason why the body part to be treated can be placed so close to the lamps 21, 22, and also why the use of synthetic plastic material is feasible for the housing 10 and/or the reflector means 30.

From a practical point of view, i.e. in consideration of the quick-tanning action or the medical-treatment efficacy which is desired, as well as from an economic point of view, the use of from two or four lamps is the most advantageous. However, it will be clear that if a lowered efficiency is acceptable, the use of a single lamp and correspondingly modified reflector means may still produce acceptable results. Conversely, if a higher construction cost is acceptable, then more than four lamps could be used. However, in either of these two cases the optimum parameters obtained by constructing the unit in accordance with the disclosure hereinbefore, would not be attainable.

Figure 3:
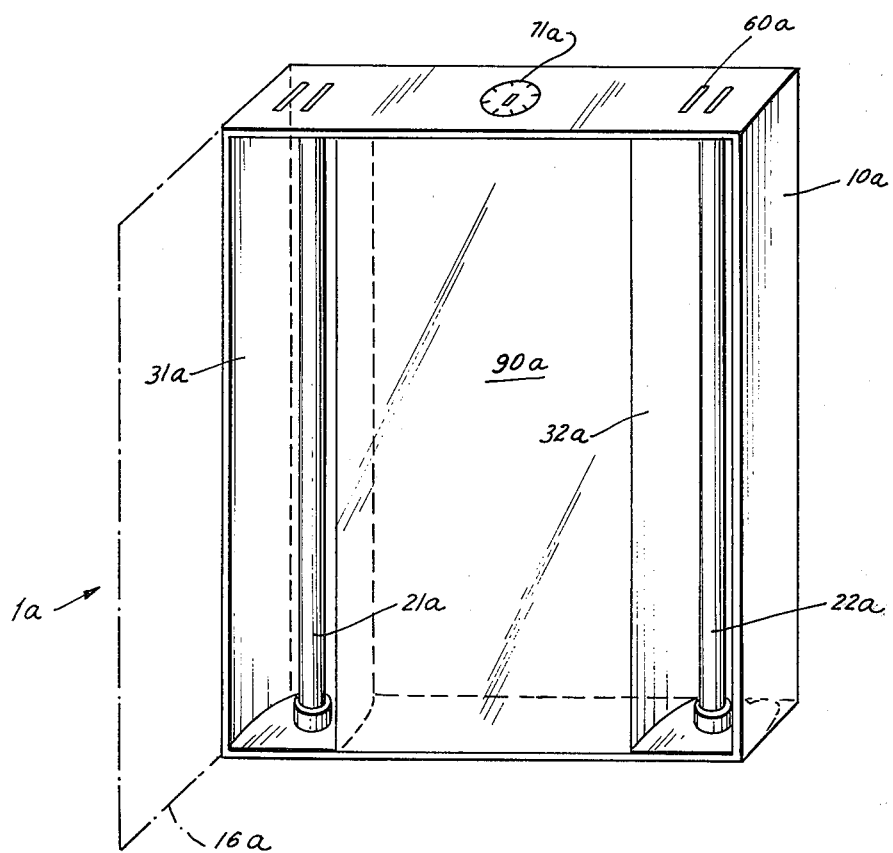
FIG. 3 is a perspective view of another modification of the apparatus of FIG. 1.

Turning now to FIGS. 3 and 4, it will be realized that the apparatus, denoted by the reference numeral 1a, is similar to that discussed above in so many respects that the same reference numerals as before, but supplemented with a letter a, are being used to identify identical or like parts. The apparatus 1a again includes a housing 10a and portions 18a and 19a which accommodate lamps 21a and 22a and are formed with reflectors 31a and 32a. Of course, the reflectors 31a and 32a could again be separate from and mounted on the housing portions 18a and 19a. However, the portions 18a and 19a are spaced from one another by a considerable distance, and a mirror 90a is so arranged in the housing 10a as to span this distance. The housing 10a may again be provided with ventilation slots 60a in the event that the reflectors 31a and 32a are separate from the housing portions 18a and 19a and form respective cooling channels therewith. Conventional circuitry, such as a starting circuit, a timing circuit of a timer 71a, or the like, can be arranged behind the mirror 90a. However, the mirror could also be mounted on the remainder of the housing 10a for pivoting about a hinge, so that a space 100a behind the mirror could be equipped with shelves or the like for storing medicinal preparations, cosmetics, toilet articles or the like thereon.

Reference character R indicates the main reflection direction of the mirror 90a, while the reference character S indicates the main radiation direction of the radiation emitted by the lamp 21a and reflected by the reflector 31a (the lamp 22a and the reflector 32a will direct radiation in a main radiation direction parallel to and spaced from the direction S). A person using the apparatus 1a and particularly the mirror 90a thereof will be located in front of the mirror 90a at a distance which varies from person to person but which lies within relatively narrow limits. The user will be subjected to the beneficial untraviolet radiation (especially within the UVA range) while observing himself or herself in the mirror 90a. This is especially true in view of the fact that the radiation emitted by the lamps 21a and 22a scatters and the person, in any event, moves his or her head relative to the apparatus 1a, especially in one or the other of the lateral directions, while looking into the mirror during shaving, teeth brushing, making up, or the like so that at least from time to time his or her head or face will be situated directly in the main radiation direction S. As shown in broken lines in FIG. 3, a lateral wall 16a (and/or 17a) may be rigidly or hingedly connected to and extend frontwardly from the housing 10a.

FIG. 5 shows a further improvement over the apparatus 1a discussed above. To differentiate and to establish cross-references between the apparatus 1, the apparatus 1a, and an apparatus 1b of FIG. 5, again the same reference numerals are being used, but followed by the letter b in this instance. A mirror 90b is here illustrated as having a concave spherical configuration or any other desirable concave shape. With the concave mirror 90b, the user has to position his or her head at a certai distance from the mirror 90b since otherwise the image seenin the concave mirror 90b would be blurred. Thus, when such a concave mirror 90b is used, the distance at which the head of the user may be located frontwardly of the mirror 90b is further restricted.

The two housing portions 18b and 19b are hinged to the central portion of the housing 10b which carries the mirror 90b by respective hinges 130b and 140b. It can then be achieved, by properly positioning the housing portions 18b and 19b, that the main radiation direction S of the emitted radiation has a component toward the mirror 90b, so that the region frontwardly of the mirror 90b and centrally thereof is permeated by a particularly high amount of the ultraviolet radiation. Of course, the direction S can be freely selected by the user to suit his or her needs, by simply pivoting the housing portions 18a and 19a about their hinges 130a and 140a to a greater or lesser extent.

Furthermore, lateral walls 16b and 17b are pivotally connected to the respective housing portions 18b and 19b by respective hinges 110b and 120b. Each of these lateral walls 16b and 17b has a reflective surface at its inside, this reflective surface being formed by an aluminum foil, an aluminum or similar layer, or the like. Because of the reflecting properties of the inner surfaces of these lateral walls 16b and 17b, they can divert a portion of the emitted radiation, which would otherwise escape, also into the above-mentioned central region frontwardly of the mirror 90b.

Additionally, the lateral walls 16b and 17b can also be light-reflective at their outer surfaces. Under these circumstances, the apparatus 1b can be used as a three-part mirror when the lateral walls 16b and 17b are pivoted in front of, and conceal, the lamps 21b and 22b and the associated reflectors 31b and 32b, provided that the lateral portions 16b and 17b have such widths as not to fully conceal the mirror 90b when so pivoted. However, it is currently preferred that each of the lateral walls 16b and 17b have a width corresponding to one-half of the width of the housing 10b (or of the distance between the hinges 110b and120b) so that, in the above-mentioned pivoted position, they will fully conceal even the mirror 90b and will give the housing 10b an esthetically pleasing parallelepiped or columnar configuration.

Figure 6:
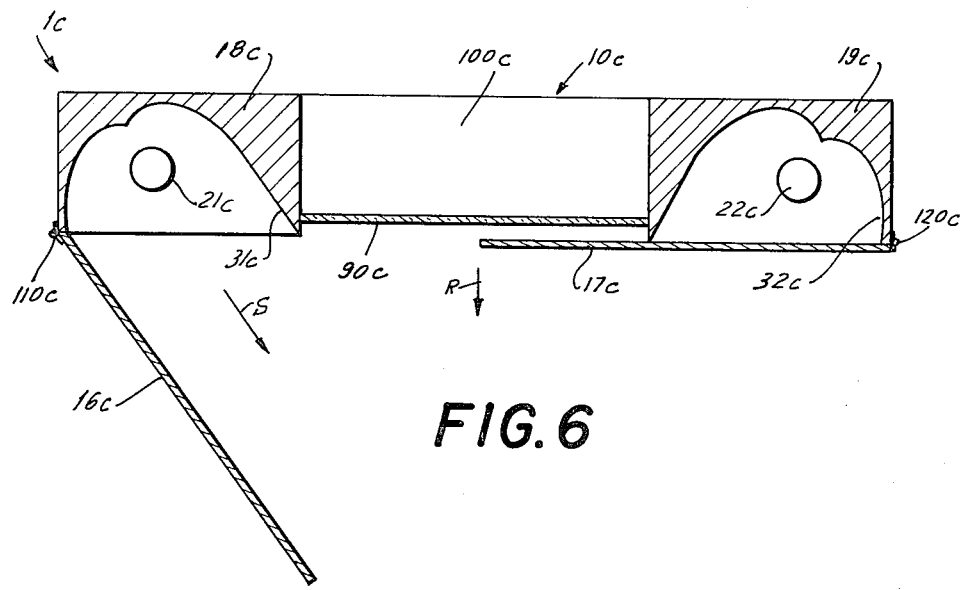
FIG. 6 is a view similar to FIGS. 4 and 5 of yet another modification of the apparatus.

For the same reasons as discussed above, a letter c has been appended to each reference numeral identifying the components of an apparatus 1c of FIG. 6. In this apparatus 1c, the reflectors 31c and 32c are built into the housing portions 18c and 19c (which are immovable relative to the central portion of the housing 10c) in angularly displaced positions about the respective axes of the lamps 21c and 22c, so that there results a main radiation direction S for each of the reflectors 31c and 32c which has a component toward the mirror 90c. The lateral walls 16c and 17c, which may be made light-reflective at their inner surfaces, serve as doors for closing the housing 10c, owing to their hinged connection to the housing portions 18c and 19c by the hinges 110c and 120c. Similarly as above, these lateral walls 16c and 17c could also be light-reflective at their outer surfaces for the same reason as discussed above.

Figure 7:
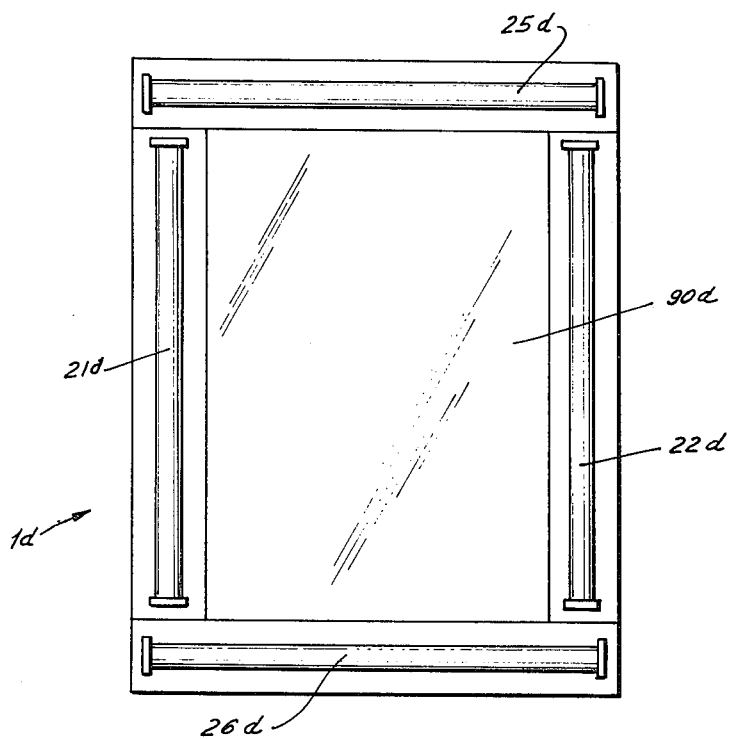
FIG. 7 is a front elevational view of a further apparatus similar to that of FIGS. 4 to 6.

Finally, parts of an apparatus 1d illustrated in FIG. 7 again are identified by the same reference numerals followed by the letter d. The apparatus 1d, which can be in all other respects similar to any other apparatus discussed above which is equipped with a mirror, employs, in addition to the two vertically extending lamps 21d and 22d (with or without the associated reflectors) laterally flanking the mirror 90d, two additional lamps 25d and 26d (again with or without associated reflectors) which are respectively arranged above and below the mirror 90d. Of course, instead of using the above-mentioned four lamps 21d, 22d, 25d, and 26d, it would also be possible, as contemplated by the present invention, to use a single lamp extending along the same or a different, for instace circular, course.

Commercially available radiating lamps, for instance of the type Philips TL/09, can be utilized in the apparatus of the present invention. Such lamps have a low-pressure mercury filling, a luminescent layer which generates a continuous spectrum in the UVA range, and an envelope which substantially absorbs the UVB and UVC radiation which may be incidentally generated during the operation of the lamp. Of course, when different lamps are to be employed where the envelope does not filter out or absorb the undesired UVB and UVC radiation, a separate filter can be used, which may be located at the exit of the reflectors, to give an example.

As already mentioned previously, this apparatus can be used not only for cosmetic, but also for medical, purposes, for instance, for the treatment of psoriasis. Under these circumstances, it may be necessary to use a lamp (or a plurality of such lamps) having a slightly different emission spectrum which generates or emits ultraviolet light even in the long-wave part of the UVB range, such as between 300 and 315 nm.

While the invention has been illustrated and described as embodied in an apparatus for producing ultraviolet radiation, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Apparatus for producing ultraviolet radiation, particularly a quick-tanning sunlamp, comprising a source of substantially uniform ultraviolet radiation, including at least two spaced-apart tubular low-pressure mercury lamps; means for intercepting at least the major percentage of wavelength bands of ultraviolet radiation below approximately 300 nm; and support means cooperating with said source and defining at least one opening for the escape of ultraviolet radiation consisting essentially of the remaining wavelength band of ultraviolet radiation, said support means including reflector means which includes for each of said lamps a trough-shaped reflector surrounding the respective lamp along at least one arc, at least one intermediate portion between adjacent ones of said lamps, and two lateral portions having zones projecting forwardly beyond said intermediate portion and spaced therefrom across the respective reflectors, said lateral portions having forward edge portions defining said opening and the space between said lateral portions and forwardly of said intermediate portion being substantially unobstructed, said source, in cooperation with said reflector means, thus establishing a high-density radiation field in the vicinity of said opening, the heat output of said lamps being sufficiently low so that the temperature in the region of said radiation field is below the range of discomfort of a person exposed to said radiation field.

2. Apparatus as defined in claim 2, wherein said source further includes at least one further lamp similar to said one lamp and mounted in said support means in registry with said opening and spaced from said one lamp; and wherein said support means includes reflector means including for each of said lamps a trough-shaped reflector surrounding the respective lamp along at least one arc, and said reflector means including at least one intermediate portion between adjacent ones of said lamps and two lateral portions having zones which project forwardly of said intermediate portion and have forward edge portions defining said opening, the space between said lateral portions and forwardly of said intermediate portion being substantially unobstructed.

3. Apparatus as defined in claim 2, wherein said lamps are closely adjacent to one another and said reflectors merge with each other in said intermediate portion.

4. Apparatus as defined in claim 2, wherein said source comprises at most two further of said lamps.

5. Apparatus as defined in claim 2, said trough-shaped reflectors each having a maximum width, and said zones of said lateral portions projecting forwardly of said intermediate portion by a distance which is substantially equal to said maximum width.

6. Apparatus as defined in claim 2, wherein said forward edge portions are transversely spaced from one another by a predetermined distance which is slightly greater than the width of a human face.

7. Apparatus as defined in claim 6, wherein said distance is between substantially 17-20 cm.

8. Apparatus as defined in claim 2, wherein said zones extend substantially parallel to each other.

9. Apparatus as defined in claim 2, wherein the height of said intermediate portion, as considered from the bottoms of the troughs of said reflectors, is sufficiently short so that direct ultraviolet radiation from each of said lamps can impinge upon that one of said lateral portions which is laterally remote from the respective lamp.

10. Apparatus as defined in claim 2, wherein the cross-sectional configuration of said reflector means includes two laterally inner arcs which constitute said intermediate portion and intersect one another at an acute angle, and two laterally outer arcs each of which defines with one of said inner arcs a trough for one of said lamps and has a laterally inner end merging with the respective inner arc midway of the trough under an obtuse angle and a laterally outer end merging tangentially with one of said zones.

11. Apparatus as defined in claim 10, wherein said zones are planar and straight.

12. Apparatus as defined in claim 2 wherein said support means includes a housing surrounding said source and reflector means and having an outlet for said ultraviolet radiation field.

13. Apparatus as defined in claim 12, said housing being of parallelepiped outline and having a front side provided with said outlet, and a rear side, lateral sides, and ends, at least some of which are configured to support said housing on a substrate.

14. Apparatus as defined in claim 12, said housing having inner wall surfaces which constitute said reflector means.

15. Apparatus as defined in claim 12, wherein said housing surrounds said reflector means and defines therewith a clearance; and further comprising venting ports in said housing communicating with said clearance.

16. Apparatus as defined in claim 12; and further comprising at least one bracket on said housing at said outlet thereof, for facilitating proper placement of body portions to be irradiated with reference to said outlet.

17. Apparatus as defined in claim 1, wherein said support means includes a housing, and at least one light-reflective portion in said housing having at least a region which extends laterally beyond said source by a distance sufficient for viewing at least most of the face of the user therein; and wherein said source emits at least the predominant part of its radiation in a direction parallel to the main reflecting direction of said region of said light-reflective surface.

18. Apparatus as defined in claim 17, wherein said light-reflective portion is a mirror.

19. Apparatus as defined in claim 17, wherein said source emits a substantial proportion of its radiation in a direction which has a component toward said region of said light-reflective portion.

20. Apparatus as defined in claim 17, wherein said source includes at least one further lamp similar to said lamp, said lamps flanking said region of said light-reflective portion at opposite sides thereof.

21. Apparatus as defined in claim 20, wherein said lamps are straight and extend substantially vertically.

22. Apparatus as defined in claim 20, wherein said lamps are straight and extend substantially horizontally.

23. Apparatus as defined in claim 22, wherein said source includes two additional lamps similar to said lamps and arranged substantially vertically at opposite sides of said region of said light-reflective portion to flank the latter.

24. Apparatus as defined in claim 17, wherein said region of said light-reflective portion has a concave spherical configuration.

25. Apparatus as defined in claim 17, wherein said support means further includes a trough-shaped reflector arranged behind said lamp as viewed through said opening, said reflector reflecting a part of the radiation emitted by said lamp in a direction which has a component toward said region of said light-reflective portion.

26. Apparatus as defined in claim 25, wherein said trough-shaped reflector is so mounted in said housing that its central plane encloses an acute angle with the plane of said opening.

27. Apparatus as defined in claim 25, wherein said housing includes a mounting portion including said light-reflective portion, and at least one additional portion mounted on said mounting portion for pivoting about an axis.

28. Apparatus as defined in claim 27, wherein said lamp and said reflector are elongated and straight and are so mounted on said additional portion of said housing as to extend substantially parallel to said axis.

29. Apparatus as defined in claim 28, wherein said housing further includes a further additional portion mounted on said mounting portion for pivoting about an axis parallel to and spaced from said axis, said axes being arranged at opposite sides of said mounting portion; and wherein each of said additional portions has a width substantially corresponding to one-half of the width of said mounting portion.

30. Apparatus as defined in claim 17, wherein said housing includes a mounting portion including said light-reflective portion, and at least one additional portion mounted on said mounting portion and extending frontwardly of said opening.

31. Apparatus as defined in claim 30, wherein said additional portion has an inner surface facing said opening and being reflective at least to ultraviolet radiation.

32. Apparatus as defined in claim 30, wherein said additional portion is pivotally connected to said mounting portion.

33. Apparatus as defined in claim 32, wherein said housing further includes a further additional portion mounted on said mounting portion for pivoting about an axis parallel to and spaced from said axis, said axes being arranged at opposite sides of said mounting portion; and wherein each of said additional portions has a width substantially corresponding to one-half of the width of said mounting portion.

34. Apparatus as defined in claim 2, said zones of said lateral portions projecting forwardly of said intermediate portion by a distance of at least 8.5 cm.

35. Apparatus for irradiating selected portions of a human body by ultraviolet radiation, particularly a quick-tanning sunlamp, comprising support means defining at least one opening at which the respective portion to be irradiated is to be situated; and means for establishing a high-density radiation field of essentially ultraviolet radiation of wavelengths exceeding approximately 300 nm at said opening of said support for irradiation of the respective portion, including a source of substantially uniform ultraviolet radiation which includes at least one tubular low-pressure mercury lamp having an output sufficiently low for the temperature in the region of said radiation field to be below the range of discomfort for a person exposed to said radiation field at said opening, and means for intercepting at least the major percentage of ultraviolet radiation wavelengths below approximately 300 nm before reaching said radiation field.

* * * * *